United States Patent [19]

Rolleston et al.

[11] 4,187,284
[45] Feb. 5, 1980

[54] SKELETAL IMAGING KIT UTILIZING TRIETHYLENE TETRAMINE HEXA (METHYLENE PHOSPHONIC ACID)

[75] Inventors: Richard E. Rolleston, Dollard des Ormeaux; Jacques A. Nadeau, Ville St. Laurent, both of Canada

[73] Assignee: Merck & Co., Inc., Rahway, N.J.

[21] Appl. No.: 838,709

[22] Filed: Oct. 3, 1977

[51] Int. Cl.$^2$ .................................................. A61K 43/00
[52] U.S. Cl. ................................ 424/1; 206/569; 260/435 R; 260/502.5
[58] Field of Search ............ 424/1; 260/502.5, 435 R; 206/569

[56] References Cited

U.S. PATENT DOCUMENTS

| | | | |
|---|---|---|---|
| 3,832,393 | 8/1974 | Krueger et al. | 260/502.5 |
| 3,974,268 | 8/1976 | Subramanian et al. | 424/1 |
| 3,983,227 | 9/1976 | Tofe et al. | 424/1 |
| 4,017,595 | 4/1977 | Subramanian et al. | 424/1 |

OTHER PUBLICATIONS

Moedritzer et al., J. Org. Chem., 31 (1966), pp. 1603–1607.
Subramanian et al., Radiopharmaceuticals, Society of Nuclear Medicine, Inc., N.Y., 1975, pp. 319–328.

*Primary Examiner*—Leland A. Sebastian
*Attorney, Agent, or Firm*—Thomas E. Arther; Mario A. Monaco; Rudolph J. Anderson, Jr.

[57] ABSTRACT

This invention relates to a novel diagnostic kit for use in radiographic bone scanning. More particularly, it relates to a kit comprising ingredients employed in the preparation of an intravenous injection of a complex of Technetium-99m, stannous ion, and an organic phosphonate identified as triethylene tetramine hexa (methylene phosphonic acid).

5 Claims, No Drawings

SKELETAL IMAGING KIT UTILIZING TRIETHYLENE TETRAMINE HEXA (METHYLENE PHOSPHONIC ACID)

BACKGROUND OF THE INVENTION

Various 99m Technetium labeled phosphate compounds have been tested for their use as bone imaging agents using a variety of radiographic bone scanning techniques. In general, the prior art methods prepared bone imaging agents by mixing a solution of Technetium-99m as the pertechnate with a freeze-dried mixture of a phosphate or a phosphonate compound and stannous chloride employed as the reducing or complexing agent. These prior art methods are referred to in detail in RADIOPHARMACEUTICALS, edited by Subramanian, Rhodes, Cooper, and Sodd, 1975, particularly in the chapter entitled, "An Evaluation of 99m TC Labeled Phosphate Compounds as Bone Imaging Agents" pp. 319-328 inclusive. This reference indicates that 99m TC labeled methylene diphosphonate is the agent of choice for bone imaging in nuclear medicine.

More recently, additional phosphonate compounds have been tested as both skeletal and myocardial infarct agents—JOURNAL OF NUCLEAR MEDICINE, June 1975, p. 540. Here there is described the use of various ethylene diamine polyphosphonic acid and, in particular, diethylene triamine penta (methylene phosphonic acid). The particular phosphonates mentioned are reported to be likely candidates for clinical use in view of the fact that they are cleared from the blood more rapidly than the agents utilized in the past.

SUMMARY OF THE PRESENT INVENTION

In accordance with the present invention, there is provided a diagnostic kit suitable for use in radiographic scanning of bone. The kit ordinarily contains sufficient material for more than one dose. It comprises a freeze-dried mixture of the components suitable for reconstitution with a solution of sodium pertechnate. The present kit employs a single container including a reducing agent and an organic compound for use in the preparation of an injectable bone imaging diagnostic kit. The kit comprises a freeze-dried mixture of a water-soluble salt of triethylene tetramine hexa (methylene phosphonic acid) and a non-toxic stannous salt.

This diagnostic kit preferably comprises a freeze-dried mixture of approximately 10 mg. of the triethylene tetramine hexa (methylene phosphonic acid) (TTHMP) and 250 mcg. of stannous chloride as the dihydrate. Although this ratio is preferred, the stannous chloride compound is effective in amounts of from 1-100 mg. of stannous chloride dihydrate mixed with 10 mg. of TTHMP.

The TTHMP used as the phosphonate component of the kit is prepared in the following manner. An aqueous solution of triethylene tetramine is treated with excess dilute hydrochloric acid to produce the tetrahydrochloride salt. This aqueous solution of salt is then added to a mixture of 6 moles of phosphorus trichloride in dilute hydrochloric acid and refluxed for a period of about one hour while adding 12 moles of formaldehyde in dropwise fashion as a 37% aqueous solution and refluxed for an additional one hour to produce the desired compound—TTHMP. The reaction mixture containing the desired product is adjusted to pH 6 with dilute sodium hydroxide and heated to the boiling point. To the boiling solution of the free acid is then added an aqueous solution of 6 moles of lead II nitrate, which furnishes a voluminous precipitate of the lead salt of the acid. The lead salt is recovered by filtration and washed with hot water. In order to remove the lead and recover the free acid, the lead salt is suspended in water, and hydrogen sulfide gas is bubbled through the solution to precipitate the lead as the sulfide and leave the TTHMP free acid in solution. The suspension of lead sulfide is removed by filtration, yielding the TTHMP free acid in solution in the filtrate. The aqueous filtrate is then reduced in volume by concentration under reduced pressure to the consistency of a thick syrup. The free acid is precipitated from the syrup by the addition of 10 volumes of ethanol. The aqueous ethanol suspension of the free acid is then concentrated under reduced pressure, leaving a yield of dry residue of precipitated TTHMP free acid, which is pulverized to a powder suitable for use in preparation of the kit.

In the process of preparing the instant diagnostic kit, it is essential that the single vial be prepared observing aseptic techniques and using normal saline solution as the diluent so that the ingredients, when reconstituted with Technetium 99m, are compatible with body fluid and may be intravenously injected without further treatment after mixing. Another important feature of the present invention is the ratio of amounts of the TTHMP and the stannous salt employed as the complexing agent. It is important to the present invention that the weight ratio of TTHMP to stannous salt is about 40:1. In preparing the components of the present kit, the first component is prepared by dissolving 40 parts by weight of TTHMP and 1 part by weight of stannous chloride dihydrate in water made slightly acid (pH 3-5) with hydrochloric acid and diluting with water to a concentration of approximately 4 mgm/ml. of TTHMP by weight, subdividing the bulk solution into individual dosage amounts and aseptically freeze drying the individual dosages to provide a readily-soluble mixture of 10 mg. TTHMP and 250 mcg. stannous chloride as the dihydrate.

The kit comprising the freeze-dried mixture of TTHMP and stannous chloride is readily employed as a diagnostic tool for skeletal imaging in the following manner. To the freeze-dried mixture of TTHMP and stannous chloride is added a solution of 2-8 ml. of a solution containing approximately 20-100 millicuries of sodium pertechnate Tc 99m. The resulting injectable solution of TTHMP-stannous complex labeled with Tc 99m can be used immediately without further treatment.

In utilizing the instant kit for skeletal imaging, an aqueous solution of from 2-8 milliliters of the required amount of sodium pertechnate Tc 99m (available as instant Technetium 99m or from a sterile generator of the type described in U.S. Pat. No. 3,369,121) is mixed with the lyophilized mixture of TTHMP and stannous chloride to form a solution of reduced pertechnate ion bound to the phosphonate compound, which solution is immediately ready for injection into the patient. Intravenous injection of approximately 10 millicuries of the Tc 99m TTHMP-stannous complex is followed by imaging of the animal skeleton in approximately 1-2 hours. The present kit is highly satisfactory because of its simplicity and is readily employed by the clinician with maximum economy of time and effort.

EXAMPLE 1

Preparation of Kit Containing a Freeze-Dried Mixture of 10 Mg. of Triethylene tetramine hexa (methylene phosphonic acid) and 250 mcg. Stannous Chloride dihydrate A solution is prepared by dissolving 100 mg. of triethylene tetramine hexa (methylene phosphonic acid) (TTHMP) and 2.5 mg. stannous chloride dihydrate in 20 ml. sterile distilled water. The pH of the solution is adjusted to 4 using concentrated hydrochloric acid and aqueous sodium hydroxide solution.

The solution is subdivided into 2 ml. portions and filled into 10 ml. vials. The subdivided solutions are then aseptically freeze-dried to provide a readily-soluble, freeze-dried mixture of 10 mg. TTHMP and 250 mcg. stannous chloride dihydrate in each vial and stored in a nitrogen atmosphere.

EXAMPLE 2

Use of Kit in Preparing Injectable Bone Imaging Solution

Approximately 2-8 ml. of a sterile saline solution of from 20-100 millicuries of sodium pertechnate TC 99m (ordinarily about 40 millicuries) is aseptically added to the contents of one of the vials described in the previous Example. The volume is adjusted to 10 ml. with sterile saline solution if desired. The resulting mixture is then shaken to provide the final dosage for TC 99m TTHMP-stannous complex suitable as an agent for imaging human or animal skeleton. This final form usually contains more than enough for one dose, ordinarily 3-5 doses containing approximately 10 millicuries per dose.

What is claimed is:

1. A kit for the preparation of an injectable solution incorporating Technetium 99m which comprises in a single sterile container a freeze-dried mixture of triethylene tetramine hexa (methylene phosphonic acid) or a water-soluble salt thereof and a water-soluble tin salt.

2. A kit for the preparation of an injectable solution incorporating Technetium 99m which comprises in a single sterile container a freeze-dried mixture of triethylene tetramine hexa (methylene phosphonic acid) or a water-soluble salt thereof and a water-soluble tin salt in a ratio by weight of from 10-100 parts of triethylene tetramine hexa (methylene phosphonic acid and 1 part of tin as stannous chloride.dihydrate.

3. A kit in accordance with claim 2 in which the weight ratio of the components is 40 parts of triethylene tetramine hexa (methylene phosphonic acid) and 1 part of tin as stannous chloride.dihydrate.

4. A kit in accordance with claim 3 in which the triethylene tetramine hexa (methylene phosphonic acid) is present as the free acid and the tin is added in the form of stannous chloride.dihydrate.

5. The lead salt of triethylene tetramine hexa (methylene phosphonic acid).